United States Patent [19]

Reineke

[11] Patent Number: 4,659,854
[45] Date of Patent: Apr. 21, 1987

[54] METHOD OF PREPARING DIALKYLPHENYLPHOSPHONATES

[75] Inventor: Karl E. Reineke, Mohegan Lake, N.Y.

[73] Assignee: Stauffer Chemical Company, Westport, Conn.

[21] Appl. No.: 869,538

[22] Filed: Jun. 2, 1986

[51] Int. Cl.$^4$ .............................................. C07F 9/40
[52] U.S. Cl. ...................................................... 558/98
[58] Field of Search ........................... 558/98, 214, 216

[56] References Cited

U.S. PATENT DOCUMENTS 2,928,859  3/1960  Preston et al. ...................... 558/104
3,408,428  10/1968  Boschan et al. ...................... 558/98

Primary Examiner—Anton H. Sutto
Attorney, Agent, or Firm—Roger S. Benjamin

[57] ABSTRACT

Dialkylphenylphosphonates are prepared by the reaction of a metal alkoxide with a phenyl phosphonic dihalide. The reactants are combined to give a temperature rise to 60° C. within 15 minutes, resulting in improved yields and assay of product.

13 Claims, No Drawings

METHOD OF PREPARING DIALKYLPHENYLPHOSPHONATES

BACKGROUND OF THE INVENTION

The alkylation of phosphonyl halides by the reaction of phosphonyl halide with an appropriate sodium alkoxide is mentioned in U.S. Pat. No. 2,928,859. Phosphonyl halide alkylations are known to proceed with highly variable yields and purity of product.

It is desirable to develop processes for preparing dialkylphenylphosphonates which give high yield and excellent purity.

FIELD OF THE INVENTION

This invention is a process for preparing organophosphonates.

SUMMARY OF THE INVENTION

Triorganophosphonates are prepared by the reaction of metal alkoxides with organophosphonic dihalides at temperatures in excess of 60° C.

DETAILED DESCRIPTION OF THE INVENTION

The triorganophosphonates prepared by the process of the invention are represented by the formula:

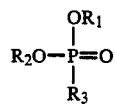

wherein $R_1$, $R_2$ and $R_3$ are the same or different hydrocarbyl or alkoxyhydrocarbyl groups Preferred products of the process of this invention are symmetrical arylphosphonates wherein $R_1$ and $R_2$ are the same alkyl group and $R_3$ is an aromatic group.

The essential reactants for the process of the invention are: (1) a soluble metal alkoxide, and (2) organophosphonic dihalide.

For the purposes of this description the metal alkoxide reactant may be considered as derived from the reaction of a metal with an alcohol as illustrated by the following chemical equation:

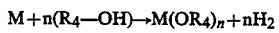

where M is a metal, $R_4$ is a hydrocarbyl group consisting of $R_1$, $R_2$ or a mixture of $R_1$ and $R_2$, and n is an integer representing the valence of the metal. Typically, the metal, M, is a monovalent metal such as lithium, sodium, or potassium. The alcohol reactant may be selected from a primary, secondary, or tertiary alcohol. The $R_4$ group of the alcohol is preferably an alkyl or alkoxyalkyl group of from 1 to 12 carbon atoms. Most preferred are alcohol reactants wherein $R_4$ is an alkyl group of from 1 to 4 carbon atoms. The product alkoxide is characterized as "soluble" if it dissolves at a level of at least 10 weight percent in the alcohol, $R_4$—OH, from which it is derivable. Particularly desirable alcohols are methanol, ethanol, propanol, and butanol.

The soluble metal alkoxide reactant employed in the process of the invention is particularly effective in promoting reaction if it is freshly prepared. For example, sodium metal is reacted with an excess of ethanol to form sodium ethoxide. The sodium ethoxide product dissolves in the excess ethanol reactant and the resultant solution may be directly employed as at least part of the reaction medium together with being a source of metal alkoxide reactant.

The second reactant is an organophosphonic dihalide represented by the formula:

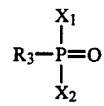

wherein $R_3$ is a hydrocarbyl radical containing 1 to 20 carbon atoms, and $X_1$ and $X_2$ are the same or different halogen radicals selected bromide or chloride or fluoride. Preferably $R_3$ is a phenyl or alkyl substituted phenyl radical. A particularly preferred second reactant is phenylphosphonic dichloride.

The reaction medium may be any non-interfering liquid in which the first and second reactants are soluble. Alcohol is a suitable reaction medium, with the proviso that the alcohol (or mixture of alcohols) used in the reaction zone correspond to the alcohols from which the first alkoxide reactant is derivable. If the alcohol constituting the reaction medium differs from the alcohol usable for formation of the alkoxide reactant than the reaction product of the second step may have new organo- groups resulting from an equilibrium with the reaction medium.

The time required for reaction is not critical and typically is in the range of from about 5 minutes to 24 hours.

The ratio of metal alkoxide first reactant and organophosphonic dihalide second reactant is limited by the requirement that at least a stoichiometric amount of the organophosphonic dihalide reactant be present in the final reaction zone mixture. The reaction may be conducted with a slight stoichiometric excess (e.g., 10% excess) of the organophosphonic dihalide reactant if desired. It is believed that excess alkoxide acts to cleave the product to yield phosphonic acid salts. Therefore, excess alkoxide in the final product should be avoided.

The reaction is exothermic and this property is used to advantage to achieve a required minimum reaction temperature of 60° C. Rapid addition and mixing of the first and second reactants in a liquid reaction medium is an effective method of effecting an in situ rapid temperature rise that encourages high yield (at least 90%) and assay (at least 90%) of the triorganophosphonate product.

It is a discovery of this invention that the yield and purity of the dialkylphosphonate product is dependent on having a reaction temperature of at least 60° C. Typically, the reaction is conducted in a temperature range of from at least 60° C. to 80° C. The upper temperature limit is not critical and is set in practice by the boiling point of the reaction medium.

The reaction should be conducted so that the reaction zone meets the process requirements of (1) having at the conclusion of the reaction at least stoichiometric proportions of the second organophosphonic dihalide reactant, and (2) the temperature of the reaction zone is raised to a minimum of 60° C. within a very short time. Generally, successful operation of the process requires that the temperature of the reaction zone be at least 60° C. within 15 minutes of mixing the reactants. The metal alkoxide reactant is added to the organophosphonic dihalide reactant at such a rate that a rapid in situ exothermic release creates and maintains a reaction zone temperature of at least 60° C. Heat may also be applied externally to the contents of the reaction zone to maintain the necessary temperature.

The conclusion of the reaction may be determined by observing a cooling of the reaction zone after all ingredients are added.

The excess alcohol employed as reaction medium is typically stripped from the product. The product may be redissolved in solvents such as toluene, cyclohexane, or heptane.

The reaction product may be purified by a number of steps such as acid wash (e.g., 4% HCl), water wash, brine wash, or NaHCO$_3$ solution wash. After drying and solvent stripping, product is typically obtained in over 90% yield with at least 90% purity. The acid number of the product is typically below 0.5 mgKOH/g.

The practice of the invention is illustrated by the following Example:

EXAMPLE

This Example illustrates the effect of reaction temperature upon the yield and purity of diethylphenylphosphonate from the reaction of sodium ethoxide and phenylphosphonic dichloride.

Example runs A, B, and C are outside the scope of the invention. Example runs D, E, F, and G correspond to the practice of the invention.

Procedure for Run A:

A one-liter three-neck flask was equipped with a mechanical stirrer, nitrogen bubbler thermometer and reflux condenser.

Ethanol was placed into the flask and sodium metal slowly added to form NaOC$_2$H$_5$. The reaction was kept at 10° C.–20° C. with an ice bath. Stirring continued until the NaOC$_2$H$_5$ was completely dissolved.

Phenylphosphonic dichloride was added gradually with ice water cooling to keep the temperature below 25° C.

Stirring continued overnight at room temperature. Excess ethanol was distilled off the following day at atmospheric pressure using an oil bath heater at 100° C.

Procedure for Run B:

The apparatus described in the "Procedure for Run A" was used in this run.

1.04 moles of sodium ethylate and 464 milliliters of ethanol were charged to the reactor flask. Phenylphosphonic dichloride was added in a controlled manner to maintain a reaction temperature of 54° C.

Procedure for Run C:

The apparatus described in the "Procedure for Run A" was used in this run.

The reaction temperature was maintained at approximately 43° C.

Procedure for Run D:

The apparatus described in the "Procedure for Run A" was used in this run.

25.5 grams of sodium pellets were slowly added to 400 milliliters of ethanol in an ice bath. The mixture was stirred overnight and heated to form a solution.

The sodium ethoxide solution was cooled in an ice bath to about 5° C. and phenylphosphonic dihalide added as rapidly as possible. The reaction zone temperature rose from 5° C. to 61° C. in eleven minutes.

Procedure for Run E:

The apparatus described in the "Procedure for Run A" was used in this run.

The phenylphosphonic dichloride was added as rapidly as possible to the sodium ethoxide solution. The temperature rose to 83° C. within three minutes.

Procedure for Run F:

A five-liter three-neck flask was equipped with a mechanical stirrer, nitrogen bubbler, thermometer and reflux condenser.

2800 grams of ethanol were placed in the flask and 23 grams of sodium slowly added. The temperature (controlled by ice bath) was allowed to reach 60° C. The mixture was stirred overnight.

The sodium ethoxide solution was cooled in an ice bath and phenylphosphonic dichloride rapidly added to achieve a temperature of 80° C. in five minutes.

Procedure for Run G:

The apparatus and method of "Procedure for Run F" was used in this run.

TABLE

| Run | Moles NaOC$_2$H$_5$ | Moles BPOD* | Max. Temp °C. | Yield** % | Remarks |
|---|---|---|---|---|---|
| A | 0.896 | 0.422 | 25 | 73 | 3 components in reaction product |
| B*** | 1.04 | 0.513 | 54 | 73 | mixed reaction product |
| C | .95 | .47 | 43 | 92 | 84% assay, toluene used as solvent |
| D | 1.08 | 0.54 | 61 | 87 | 99% assay (no toluene) |
| E | 1.03 | 0.51 | 83 | 93 | 97% assay, toluene used as solvent |
| F | 6.88 | 3.44 | 80 | 92 | 98% assay, toluene used as solvent |
| G | 7.2 | 3.6 | 80 | 94 | 95% assay, toluene used as solvent |

*BPOD = phenylphosphonic dichloride
**Yield not corrected for assay.
***Commercial NaOC$_2$H$_5$ used.

Experiments D, E, F and G corresponding to the practice of the invention have high yield (87% to 93%) and high assay (all over 90%).

Experiments A, B, and C have mixed reaction product or product having an assay lower than 90%.

I claim:

1. A method of preparing a triorganophosphonate represented by the formula:

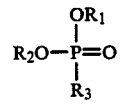

wherein R$_1$ and R$_2$ and R$_3$ are the same or different organo- radicals; and
   wherein the process comprises mixing in a liquid reaction medium; (1) a soluble metal alkoxide reactant with; (2) at least a stoichiometric amount of an organophosphonic dihalide reactant, with the proviso that the reactants are mixed at a rate sufficient to cause a temperature rise to at least 60° C. within 15 minutes.

2. The method of claim 1 wherein R$_3$ is an aromatic radical and R$_1$ and R$_2$ are alkyl radicals.

3. The method of claim 2 wherein R$_3$ is selected from phenyl and alkylated phenyl radicals of from 6 to 20 carbon atoms, and $R_1$ and $R_2$ are alkyl radicals of 1 to 12 carbon atoms.

4. The method of claim 1 wherein the soluble metal alkoxide is an alkoxide of an alkali metal.

5. The method of claim 4 wherein the soluble alkoxide is a sodium alkoxide, potassium alkoxide, or lithium alkoxide.

6. The method of claim 5 wherein the alkoxide is sodium ethoxide.

7. The method of claim 6 wherein the sodium ethoxide is prepared by the reaction of sodium metal and ethanol just prior to its reaction with the organophosphonic dihalide.

8. The process of claim 1 wherein the organophosphonic dihalide is phenylphosphonic dichloride.

9. The process of claim 1 wherein the liquid reaction medium comprises an alcohol.

10. The process of claim 9 wherein the alcohol in the reaction medium is identical to the alcohol suitable for deriving the metal alkoxide reactant.

11. The process of claim 1 wherein the reaction is conducted at a temperature of from 60° C. to about 80° C.

12. The process of claim 1 wherein the organophosphonic dihalide reactant is represented by the formula:

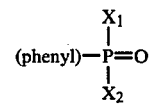

wherein $X_1$ and $X_2$ are the same or different halogen radicals.

13. A process for preparing diethylphenylphosphonate by reacting in a first step sodium metal with a stoichiometric excess of ethanol, then reacting the first step reaction mixture with at least a stoichiometric amount of phenylphosphonic dichloride; with the proviso that the reactants are combined at a rate sufficient to raise the reaction zone to at least 60° C. within 15 minutes.

* * * * *